United States Patent [19]

Lewis et al.

[11] 4,293,547

[45] Oct. 6, 1981

[54] METHOD OF TREATING MALARIA

[75] Inventors: Charles Lewis, Kalamazoo Township, Kalamozoo County; Robert D. Birkenmeyer, Comstock Township, Kalamazoo County, both of Mich.

[73] Assignee: The Upjohn Company, Kalamazoo, Mich.

[21] Appl. No.: 180,986

[22] Filed: Aug. 25, 1980

[51] Int. Cl.³ .................... C07H 15/16; A61K 31/71
[52] U.S. Cl. .................................... 424/180; 536/11; 424/181
[58] Field of Search ................... 424/180, 181; 536/11

[56] References Cited

U.S. PATENT DOCUMENTS

| | | | |
|---|---|---|---|
| 3,817,979 | 6/1974 | Argoudelis et al. | 536/11 |
| 3,856,943 | 12/1974 | Birkenmeyer | 536/11 |
| 3,892,729 | 7/1975 | Birkenmeyer | 536/11 |

*Primary Examiner*—Johnnie R. Brown
*Attorney, Agent, or Firm*—Roman Saliwanchik

[57] ABSTRACT

A process for treating a protozoan disease, for example, malaria, by the systemic administration to a subject hosting a malarial parasite of a novel analog of the well-known antibiotics lincomycin and clindamycin. These analogs are prepared by condensing a cyclic acid with a sugar amine.

34 Claims, No Drawings

METHOD OF TREATING MALARIA

DESCRIPTION

BRIEF SUMMARY OF THE INVENTION

This invention relates to the prophylactic and therapeutic treatment of subjects hosting a protozoan parasite by the systemic administration of compounds of the formula

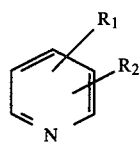   I wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive and isomeric forms thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof, wherein $R_2$, which can be singly substituted in any position of the pyridine ring not already substituted by $R_1$, is

and X is the amino function of a compound selected from the group consisting of 7(S)-halo-methyl 1-thio-α-lincosaminide and 7(R)-halo-methyl 1-thio-α-lincosaminide; and the pharmaceutically acceptable acid addition salts thereof, and to the use of compounds of the formula:

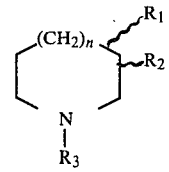   II wherein $R_1$ can be singly or multiply substituted in the ring on the same or different carbons, and $R_2$, which can be in the 2, 3, 4, 5, 6, 7, 8 or 9 position of the ring, are as defined above; wherein $R_3$ is selected from the group consisting of H, $CH_3$, $C_2H_5$, and $-CH_2-CH_2-OH$; wherein n is an integer of from 1 to 4, inclusive; and the pharmaceutically acceptable acid addition salts thereof.

Compounds of particular importance in the subject invention process are of the formula:

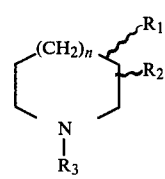   III wherein $R_1$ is in the 4 position and is alkyl of from 1 to 8 carbon atoms, inclusive, and isomeric forms thereof; wherein $R_3$ is as defined above; wherein $R_2$ is in the 2 or 3 position and is otherwise as defined above; wherein n is 1; and the pharmaceutically acceptable acid addition salts thereof.

Other compounds in the subject invention process have the formula

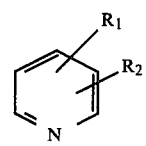   IV wherein $R_1$ and $R_2$ are as defined immediately above.

The synthesis of the analogs described herein can be shown in exemplary form as follows:

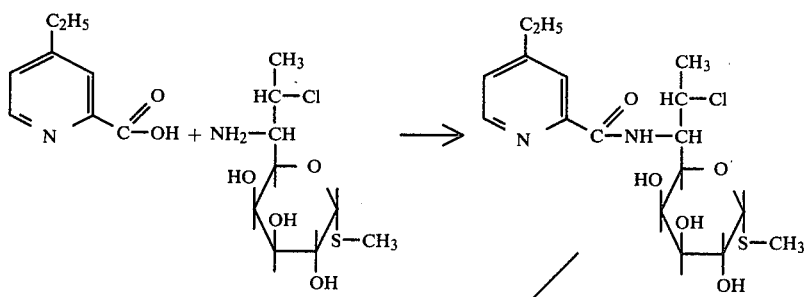

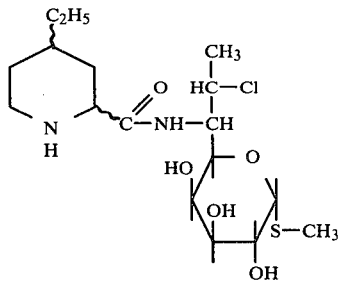

The wavy lines denote either the D-cis or L-cis isomer.

An alternate procedure which may be used to synthesize the analogs described herein can be shown in exemplary form as follows:

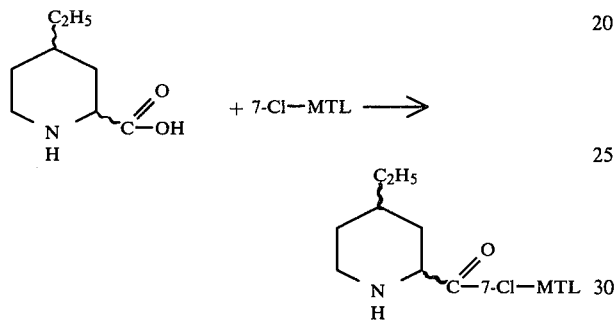

The wavy line denotes either the D-cis, L-cis, D-trans or L-trans structures.

The L-cis structure

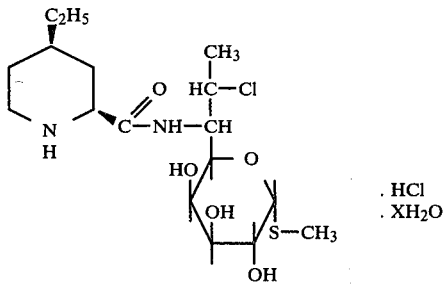

has been shown to be 5 to 10 times more active than clindamycin against *S. aureus* and *S. hemolyticus* in laboratory mice.

An isomer of V may be isolated from the above reaction and is presumed to be the D-cis compound, VA. The D-cis structure is not as potent an antibacterial agent as the L-cis compound.

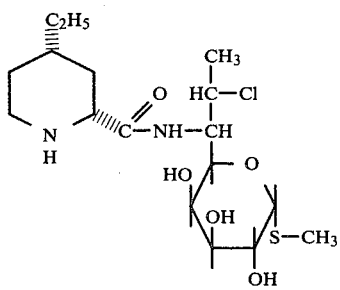

Also within the scope of the subject invention are the use of compounds of the formulae

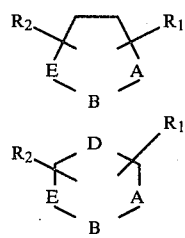

wherein A, B, D and E are selected from the group consisting of nitrogen, oxygen, sulfur and $CR_1R_1$; $R_1$ and $R_2$ are as defined previously and can be attached to any ring carbon or nitrogen atom; $R_1$ can be multiply attached to any ring carbon atom, and the pharmaceutically acceptable acid addition salts thereof.

Further, this application relates to the use of novel 2-phosphates and 2-palmitates wherein the substitution is attached to the oxygen atom and at the 2 position of the sugar ring of the above compounds.

DETAILED DESCRIPTION

It has been found in accordance with the present invention that the systemic administration of a compound of the above formulas to a subject hosting a protozoan parasite provides effective suppressive treatment of the disease. For example, when the protozoan is a malarial parasite, the subject can be animal, e.g., mice infected with *P. berghei;* birds, e.g. ducks infected with *P. lophurae* and chicks infected with *P. gallinaceum,* and mammals such as primates, e.g., monkeys infected with *P. cynomolqi,* and humans infected with *P. falciparum, P. vivax,* and *P. malariae.*

The compounds of the formulas can be administered systemically by the oral and parenteral routes preferably in association with a pharmaceutical carrier or in the case of animals (orally) in association with the animals feed. Additionally, the compounds of the formulas can be mixed with table salt for administration to humans for use in a program of mass drug administration in developing countries.

Advantageously, the compounds of the formulas do not exhibit cross-resistance when used against drug resistant, e.g., chloroquine or dimethyldiphenylsulfone (DDS), strains of malarial parasites.

The process of the present invention is accomplished by oral or parenteral administration of pharmaceutical compositions preferably presented for administration to humans and animals in unit dosage forms, such as tablets, capsules, pills, powders, granules, sterile parenteral solutions or suspensions, and oral solutions or suspensions, and oil-water emulsions containing suitable quantities of a compound of the formulas in the form of the free base, or its pharmacologically acceptable salts.

For oral administration, either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol, cellulose acetate phthalate, styrene maleic acid copolymer and the like. Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the compound of the formulation with an inert pharmaceutical diluent and filling the mixture into a hard gelatin capsule of appropriate size. In another embodiment, capsules are prepared by filling hard gelatin capsules with polymeric acid coated beads containing a compound of the formulas. Soft gelatin capsules are prepared by machine encapsulation of a slurry of a compound of the formulas with an acceptable vegetable oil, light liquid petrolatum or other inert oil.

Fluid unit dosage forms for oral administration such as syrups, elixirs, and suspensions can be prepared. The water-soluble forms of a compound of the formulas can be dissolved in an aqueous vehicle together with sugar, aromatic flavoring agents and preservatives to form a syrup. An elixir is prepared by using a hydroalcoholic (ethanol) vehicle with suitable sweeteners such as sucrose together with an aromatic flavoring agent. Suspensions can be prepared of the insoluble forms with a syrup vehicle with the aid of a suspending agent such as acacia, tragacanth, methylcellulose, and the like.

For parenteral administration, fluid unit dosage forms are prepared utilizing a compound of the formulas and a sterile vehicle, water being preferred. The compound, depending on the form and concentration used, can be either suspended or dissolved in the vehicle. In preparing solutions, a water-soluble form of a compound of the formulas can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the powder prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. For sustained action, an intramuscular suspension is prepared with an insoluble form such as the trimethylsilyl ether or the pamoate salt. Advantageously, a surfactant or wetting agent is included in the composition to facilitate uniform distribution of the compound.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, pills, troches, suppositories, powder packets, granules, wafers, cachets, teaspoonfuls, tablespoonfuls, dropperfuls, ampuls, vials, segregated multiples of any of the foregoing, and other forms as herein described.

In addition to the administration of a compound of the formulas as the principal active ingredient of compositions for treatment of malaria, the said compound can be included with other antimalarials to obtain advantageous combinations of properties. Such combinations include a compound of the formulas with quinine; with dimethyldiphenylsulfone; the 4-aminoquinolines, for example: amodiaquine, amopyroquine, cycloquine, chloroquine, hydroxychloroquine, oxychloroquine, and sontoquine; the 9-aminoaeridines, for example: quinacrine azacrine, and aminoacrichine; the 8-aminoquinolines, for example: pamaquine, fourneau 710, certuna, pentaquine, isopentaquine, primaquine, and quinocide; the biguanides, for example: proguanil, chloroproguanil, and chloroazine; the diaminopyrimidines, for example: pyrimethamine; the long-acting sulfonamides, for example: sulfadiazine, sulphormethoxine, sulfadimethoxine, and sulfamethoxypyridazino.

The dosage of the formulas for treatment depends on route and frequency of administration; the age, weight, and condition of the patient; and the particular malaria parasite to be treated. A daily dosage schedule of from about 0.5 to 200 mg/kg parenterally and from 1 to 300 mg/kg orally embraces the effective range for treatment. The preferred dosage range is from 5 to 50 mg/kg parenterally and 25 to 100 mg/kg orally. The oral suppressive dose can be as low as one-tenth the above treatment dose.

A compound of the formulas is compounded with a suitable pharmaceutical carrier in unit dosage form for convenient and effective administration. In the preferred embodiments of this invention, the dosage units contain 10, 25, 50, 100, 250, and 500 mg amounts of a compound of the formulas for systemic treatment; 5 to 65 percent w/v for parenteral treatment. The dosage of compositions containing a compound of the formulas and one or more other active ingredients is to be determined with reference to the usual dosage of each such ingredient.

Preparation of The Compounds Used In the Invention Process

Upon reacting an aminoacid of the formula

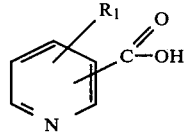

wherein $R_1$, which can be singly or multiply substituted in any position of the pyridine ring not already substituted by

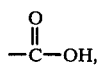

is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl and substituted phenyl; $—(CH_2)_n—OH$, $—(CH_2)_n—NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof, wherein

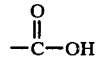

which can be singly substituted in any position of the pyridine ring not already substituted by $R_1$, with a sugar amine compound selected from the group consisting of 7(S)-halo-methyl 1-thio-α-lincosaminide and 7(R)-halomethyl 1-thio-α-lincosaminide, there are obtained the compounds of formula I.

Upon reacting an amino acid of the formula

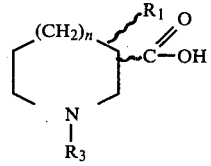

wherein $R_1$ and the position of substitution of

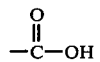

are as defined above; wherein $R_3$ is selected from the group consisting of H, $CH_3$, $C_2H_5$, and $—CH_2—CH_2—OH$; wherein n is an integer of from 1 to 4, inclusive, with a sugar amine compound, as defined above, there are obtained the compounds of formula II.

Upon reacting an acid of the formulae

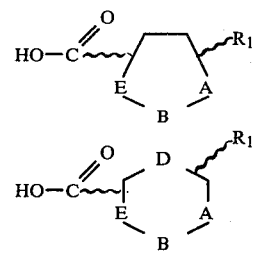

wherein A, B, D and E are selected from the group consisting of nitrogen, oxygen, sulfur and $CR_1R_1$; $R_1$ is as defined previously and can be attached to any ring carbon or nitrogen atom; $R_1$ can be multiply attached to any ring carbon atom;

can be attached to any ring carbon or nitrogen atom, with a sugar amine compound selected from the group as defined above, there are obtained the compounds of formulae VI and VII.

7-Cl-MTL is methyl 7(S)-7-deoxy-7-chloro-1-thio-α-lincosaminide of the formula

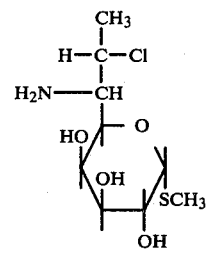

epi-7-Cl-MTL is methyl 7(R)-7-deoxy-7-chloro-1-thio-α-lincosaminide of the formula

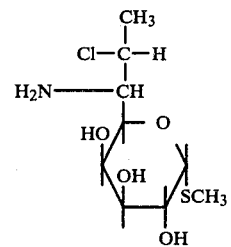

The halo group at the 7 position of the above formulas can be shown as follows

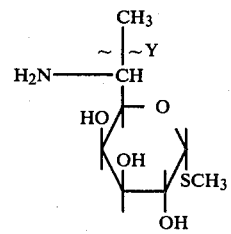

wherein Y is selected from the group consisting of 7(S)-halo and 7(R)-halo.

When a pyridine acyl group is used, the resulting analog can be reduced to give a mixture of the corresponding saturated compounds, one of which is the L-cis isomer. Other compounds which may be present include the L-trans, D-cis, and D-trans isomers. Generally, for any of the compounds described herein, the reduced form is more antibacterially-active than the unsaturated precursor. The use of a piperidine acyl group gives analogs existing as D-cis, L-cis, D-trans, and L-trans isomers.

The general method used herein to prepare the analogs is the well known process wherein an appropriate acid is coupled with an appropriate sugar amine. ("Mixed Carboxylic Acid Anhydride Procedure," Chemistry of the Amino Acids, Vol. 2, p. 970, John Wiley and Sons, Inc., 1961.) When the acid is unsaturated, the resulting unsaturated analog can be catalytically reduced under standard conditions to prepare the saturated analog. For example, the reduction can be conducted using the following conditions:

H₂ at 5 to 50 psi
Catalyst—platinum oxide (PtO₂)
Solvent—H₂O or H₂O+MeOH, or H₂O+EtOH
HCl—10% excess
Time—24 to 48 hours As used herein, alkyl of 1 to 8 carbon atoms, inclusive, and isomeric forms thereof, includes methyl, ethyl, propyl, butyl, pentyl, hexyl, heptyl, octyl, and branched chain isomers thereof.

Substituted alkyl means the above alkyl compounds in which one or more of the hydrogen atoms has been replaced by a halogen, i.e., Cl, Br, F, and I, oxygen, hydroxyl, amine (primary), amine (secondary-alkyl substituted by alkyl as above), amine (tertiary-alkyl substituted by alkyl as above), sulfur, -SH, and phenyl. Exemplary compounds are 1-fluoroethyl, 1-chloroethyl, 2-fluoroethyl, 2-chloroethyl, 1-bromopropyl, 2-iodopropyl, 1-chlorobutyl, 4-fluorobutyl, and 4-chlorobutyl.

Cycloalkyl means cyclopropyl, cyclobutyl, cyclopentyl, cyclohexyl, cycloheptyl and cyclooctyl.

Substituted cycloalkyl means a cycloalkyl substituted as above for substituted alkyl. Exemplary compounds are 2-cyclopropylethyl, 3-cyclobutylpropyl, 4-cyclopentylbutyl, and 4-cyclohexylbutyl.

Aromatic means phenyl and substituted phenyl wherein one or more of the hydrogen atoms has been replaced by a halogen, as above, hydroxyl, amine (primary, secondary, and tertiary with the latter two alkyl substituted as above), -SH, and phenyl. Exemplary compounds are p-bromophenyl, m-iodophenyl, o-chlorophenyl, p-ethylphenyl, m-propylphenyl, o-methylphenyl, and p-octylphenyl.

As detailed infra, the compounds used in the invention process can be phosphorylated to give the 2-phosphate, and acylated to give the 2-palmitate which are both antimalarially active in vivo.

Substituted oxygen means oxygen substituted by an alkyl of from 1 to 8 carbons, inclusive, aryl, and substituted aryl.

Substituted nitrogen means nitrogen substituted by an acyl of from 2 to 18 carbon, a monoalkyl of 1–8 carbons, inclusive, and a dialkyl, wherein the alkyl is from 1 to 8 carbons, inclusive, including the isomeric forms for all acyl and alkyl groups.

Halo means chloro, bromo, iodo, or fluoro.

Exemplary sources for the amino acids used as starting materials herein are as follows:

1. Heterocyclic Compounds, Vol. 1, John Wiley and Sons, Inc., 1950. This source describes the preparation of halogen and alkyl substituted amino acids.
2. Chem. Abstracts:
   81—105223A—alkyl and cycloalkyl
   81—152243S—alkyl and halogen substituted
   82—170746H—halogen substituted
   85—46322Q—dihalo substituted
   85—177258W—dihalo substituted
   84—116928X—dihalo substituted
   81—3737d—phenyl substituted
   78—58201t—phenyl substituted
   76—126800y—tetrahalo substituted
   82—11036K—bromo substituted
   83—27119W—bromo substituted
   84—16613X—bromo substituted
   78—123494G—bromo substituted 84 - 135488V - 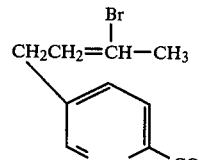

81 - 151951J - 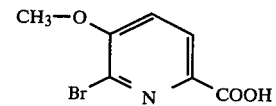

81 - 77809a - 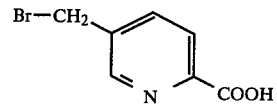

84 - 30918G - 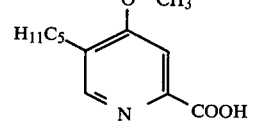

81 - 33139C - 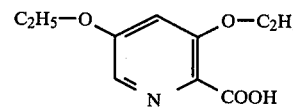

79 - 19109V - 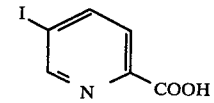

81- 3737D - 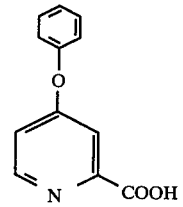

81 - 135964K - 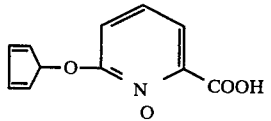

85 - 177349B - 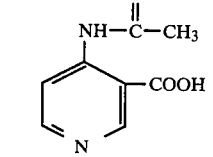

-continued

78 - 718656 - 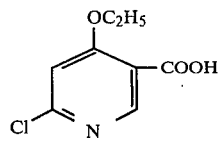

81 - 135964K - 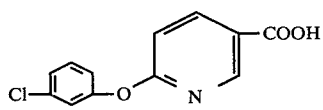

83 - 147397G - 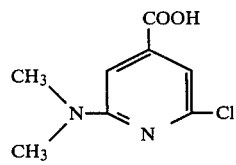

82 - 11036K - 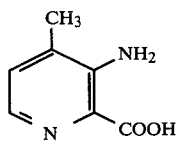

84 - 116928X - 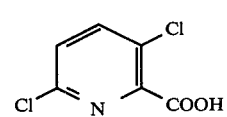

81 - 33139C - 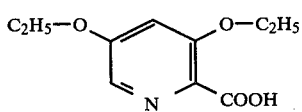

76 - 126800Y - 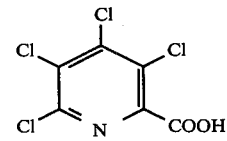

79 - 115449b - 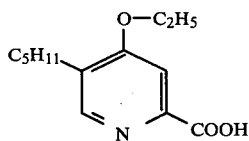

67 - 63229K - 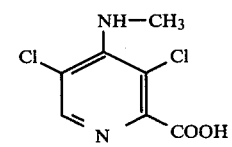

68 - 104926b - 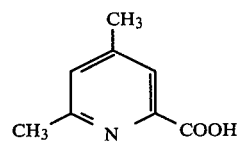

69 - 59048Z - 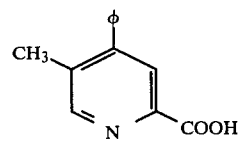

71 - 124907M - 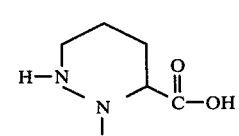

-continued

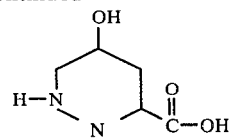

68 - 59465N - 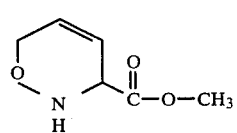

This compound can be hydrolyzed to the acid by means well known in the art, which acid can then be reduced, also by means well known in the art.

86 - 106501e - 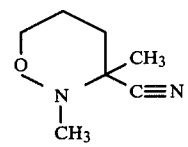

This compound can be hydrolyzed to the acid by means well known in the art. The resulting acid then can be N-demethylated by the procedures disclosed in U.S. Pat. No. 3,583,972.

69 - 67282M - 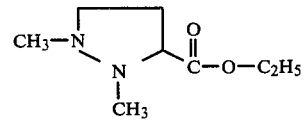

This compound can be hydrolyzed to the acid by means well known in the art.

90 - 70297-14-Z - 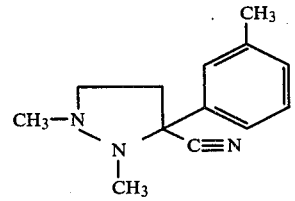

This compound can be hydrolyzed to the acid by means well known in the art. Also, one or both of the N-CH$_3$ groups can be removed from the resulting acid by following the procedures disclosed in U.S. Pat. No. 3,583,972.

90 - 168488X - 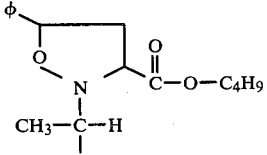

This compound can be hydrolyzed to the acid by means well known in the art. The resulting acid can be converted to the following compound

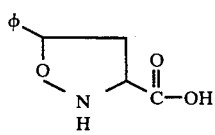

by methods disclosed in U.S. Pat. No. 3,583,972.

85 - 142995G - 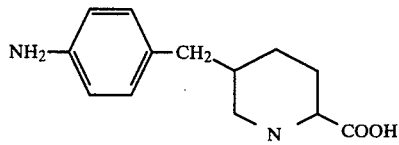

81 - 152020S - 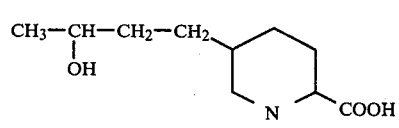

75 - 110156M - 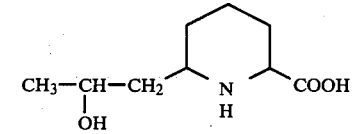

Compounds having free NH$_2$ or OH groups will have to have these groups protected before being condensed with the amino sugar. Protection of such groups is well known in the art. See Protective Groups in Organic Chemistry, J. F. W. McOmie, Plenum Publishing Co., Ltd., 1973.

3. Jour. Chem. Soc. 1969-2134-Various H-alkyl substituted pyridines

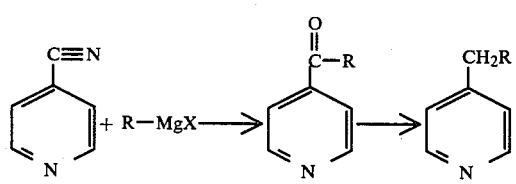

(commercially available)
R=alkyl, branched alkyl and cycloalkyl

4. Jour. Chem. Soc. 1969-934-

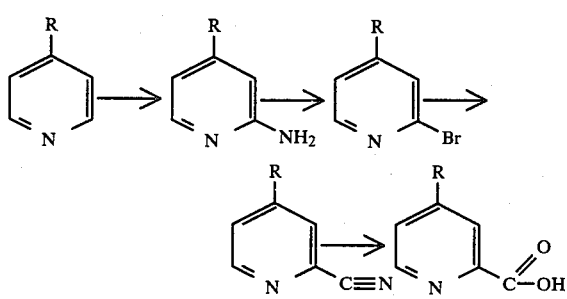

Preparation I—4-Cis-ethyl-L-pipecolic acid amide of 7-Cl-MTL.HCl (U-57,930E-Compound V)

PART I

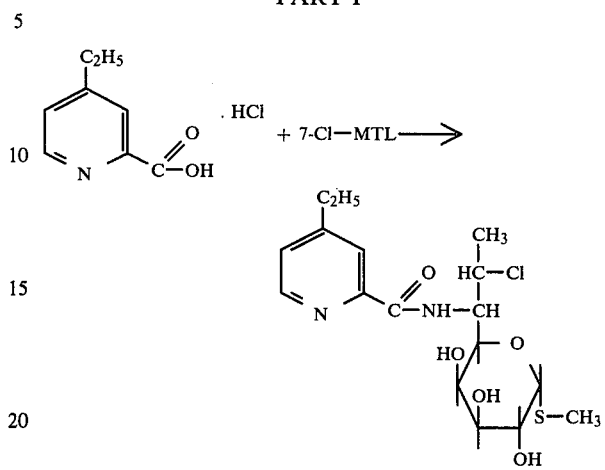

A solution of 67 g (0.357 moles) of the amino acid HCl (C.A. 51, 1643a, 1957) and 71.5 g (0.714 moles) of triethylamine dissolved in 2.5 liters of acetonitrile is cooled to 10° C. and 47.6 g (0.354 moles) of isobutylchloroformate added in one portion. This mixture (Solution A) is stirred at 10° C. for 1 hour. Solution B is made up by dissolving 97.7 g (0.357 moles) of 7-Cl-MTL (J. Med. Chem., 12-780, 1969, B. J. Magerlein and F. Kagan) in a warm mixture of 1500 ml of acetone and 1500 ml of H$_2$O. Solution B is cooled to 30° C. and added in one portion to Solution A. The reaction is stirred at 25° C. for 18 hours and the acetone and acetonitrile removed under vacuum. The white, mushy residue is filtered and the crystalline material collected and dried to give 95 g of pure product. Workup of the filtrate (chromatography) gave another 10 g of product. The overall yield is 73%. Anal. Calcd. for C$_{17}$H$_{25}$ClN$_2$O$_5$B$_5$S: C, 50.42; H, 6.22; N, 6.92; S, 7.92; Cl, 8.76. Found: C, 50.67; H, 6.40; N, 6.64; S, 7.90; Cl, 8.70. $[\alpha]_D^{CHCl_3}$ (C, 1.0)+293°

PART II

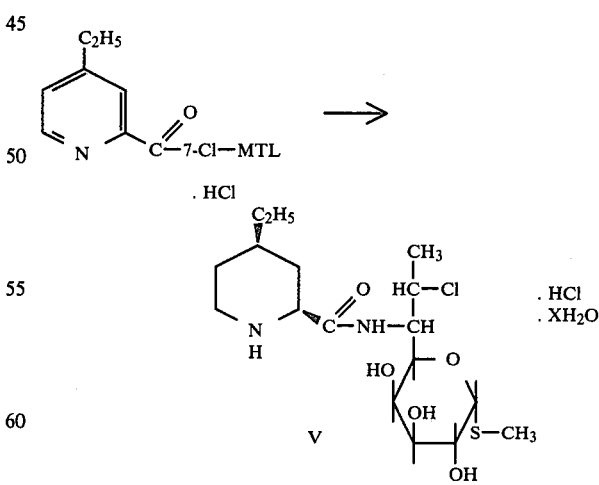

A mixture of 4.05 g (0.01 mole) of starting material, 40 ml of water, 60 ml of methanol, 1.0 ml of 37% HCl and 8.0 g of PTO$_2$ catalyst were reduced on a Parr hydrogenator at 50 p.s.i. for 3 hours. Analysis of the reaction mixture by TLC on silica gel plates in a system composed of CHCl$_3$:methanol (6:1) showed that all of the starting material was gone and that two more polar materials were present in a ratio of about 1:1. The reaction was filtered to remove the catalyst and the filtrate concentrated under vacuum to give a white crystalline mush. This was filtered and the filtrate saved. The white solid, which was the most polar of the two products observed upon TLC of the reduction mixture, was recrystallized from water to give the desired product, U-57,930E, m.p. 222°–224°, in a yield of from 25 to 35%.

Anal. Calcd. for C$_{17}$H$_{32}$Cl$_2$N$_2$O$_5$S: C, 45.63; H, 7.21; N, 6.26; S, 7.17; Cl, 15.85: Found: C, 45.77; H, 7.44; N, 6.39; S, 7.21; Cl, 16.17: $[\alpha]_D^{H2O}$ (C, 1.0)+176°.

The absolute configuration and stereochemistry of V was established by X-ray crystallography.

Also isolated from Preparation I, Part II, is compound V A. This material is obtained as follows:

The filtrate which was saved from Part II was concentrated to dryness under vacuum, the residue converted to its free base and chromatographed over silica gel using CHCl$_3$:methanol (6:1) as the eluting solvent. In this manner the least polar material mentioned in Part II was obtained. It was converted to its HCl salt and recrystallized from acetone and water. This isomer is tentatively being assigned structure V A.

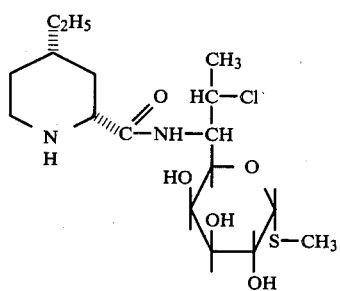

V A

Epimerization of the carbonyl function attached to the piperidine ring of V and V A may be accomplished by methods well known to those skilled in the art. The trans isomers V B and V C produced by these epimerizations may be isolated by conventional procedures such as crystallization or chromatography.

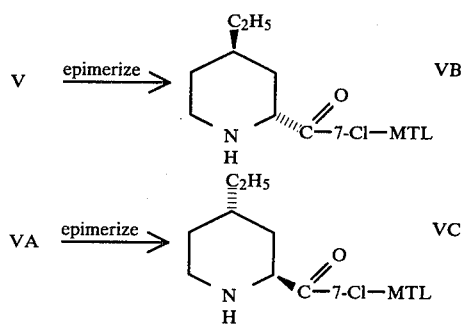

Alternatively, V and V A may be hydrolyzed to give the amino acids V D and V E which may then be epimerized by methods well known to those skilled in the art to V F and F G, respectively. The amino acids V F and V G may be coupled with any of the lincosaminides described earlier.

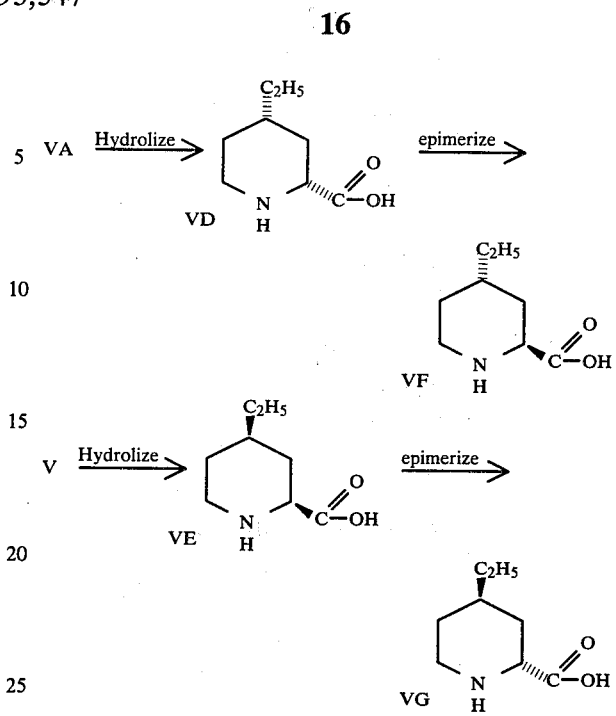

Preparation 2—Other Analogs of 7-Cl-MTL

By following the procedures of Preparation 1, but substituting the amino acid with the following amino acids there are prepared the corresponding analogs as their free bases or acid addition salts. The latter can be prepared by methods well known to those skilled in the art.

| Amino Acid | Analog |
|---|---|
| pyridine-2-COOH | U-45,863 |
| pyridine-3-COOH | U-46,138 |
| pyridine-4-COOH (HO—C=O) | U-46,137 |
| piperidine-2-COOH | U-46,337 (Fast isomer on TLC—MeOH: CHLL 95:5. Run on silica gel plates) |
| piperidine-2-COOH | U-46,465 (Slow isomer on TLC) |
| N-methyl piperidine-2-COOH | U-46,699 (Slow isomer on TLC, prepared from U-46,465) |

-continued

| Amino Acid | Analog |
|---|---|
| H₅C₂-pyridine-COOH | U-45,656 |
| C₂H₅-pyridine-COOH | U-45,652 |
| C₂H₅-piperidine(N-CH₃)-COOH | U-46,701 |
| C₂H₅-piperidine(NH)-COOH | U-60,481 |
| piperidine(N-CH₂CH₂OH)-COOH | U-44,469 |
| pyridine-COOH with Cl | U-45,657 |

Preparation 3—Analogs of epi-7-Cl-MTL

By following the procedures of Preparation 1, but substituting the amino acid with the following amino acids, and substituting epi-7-Cl-MTL for 7-Cl-MTL, there are prepared the corresponding analogs.

| Amino Acid | Analog |
|---|---|
| pyridine-COOH | Compound C |
| C₂H₅-pyridine-COOH | Compound D |
| piperidine(NH)-COOH | Compound E |
| C₂H₅-piperidine(NH)-COOH | Compound F |

Epi-7-Cl-MTL can be prepared by the procedure used to prepare 7-Cl-MTL with the exception that the starting material is epi-MTL instead of MTL.

Preparation 4—Fusaric Acid Amide of 7-Chloro-MTL.

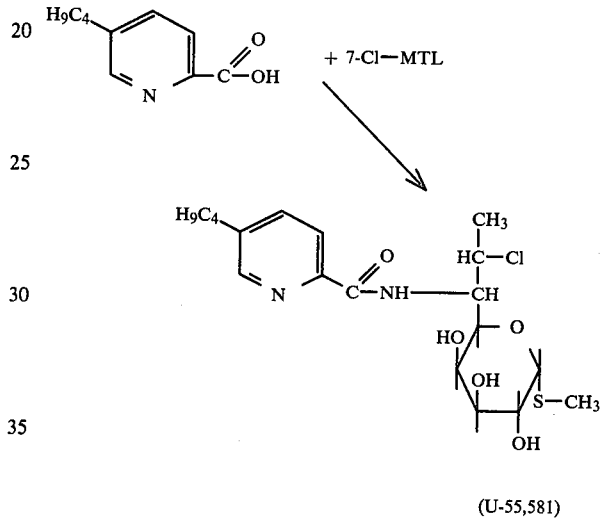

(U-55,581)

By following the procedure of Preparation 1, but substituting the amino acid with fusaric acid, there is obtained U-55,581.

Anal. Calcd. for $C_{19}H_{29}ClN_2O_5S$: C, 52.70; H, 6.75; N, 6.47; S, 7.41; Cl, 8.19. Found: C, 52.15; H, 6.65; N, 7.21; Cl, 7.94.

Preparation 5—4-Cis-n-Butyl-L-Pipecolic Acid Amide of 7-Cl-MTL or U-60,970E

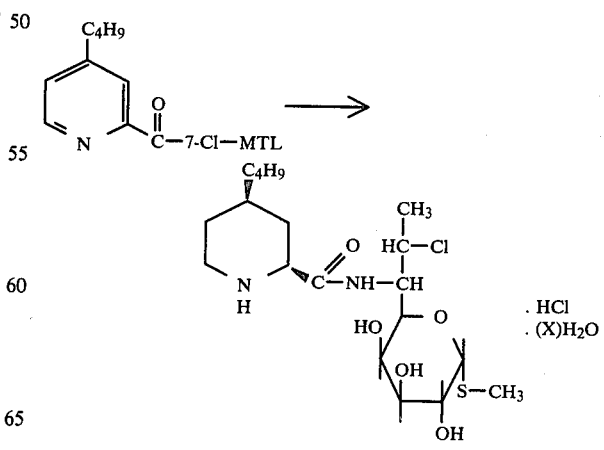

$(C_{19}H_{36}Cl_2N_2O_5S \cdot (X)H_2O)$

A mixture of 4.0 g (0.0093 mole) of starting material, 40 ml of water, 40 ml of methanol, 2 ml of 37% HCl, and 8.0 g PtO₂ catalyst were reduced on a Parr hydrogenator at 50 psi for 18 hours. The reaction was filtered to remove the catalyst and the filtrate concentrated under vacuum to give an amber oil. The oil was dissolved in 20 ml of a 2:1 solution of CHCl₃ and methanol and enough triethylamine added to neutralize the HCl present. This solution was then chromatographed over silica gel using a solvent system composed of CHCl₃:methanol (2:1). Two main product fractions are obtained. The fractions containing the faster moving material were pooled and evaporated under vacuum to give a white solid, fraction A. The fractions containing the slower moving material were pooled and evaporated under vacuum to give a white solid, fraction B. Fraction B was dissolved in a small amount of H₂O and enough 37% HCl added to make the pH 2. Crystallization occurred. The solid was collected and recrystallized from H₂O to give white crystals of the desired product, U-60,970E, m.p. 224°–226° in a yield of 25–35%.

Anal. Calcd. for $C_{19}H_{36}Cl_2N_2O_5S$: C, 47.99; H, 7.63; N, 5.89; S, 6.75; Cl, 14.92: Found: C, 47.97; H, 7.42; N, 6.23; S, 6.90; Cl, 14.87.

Preparation 6—4-Cis-n-Butyl-D-Pipecolic Acid Amide of 7-Cl-MTL or U-61,734E

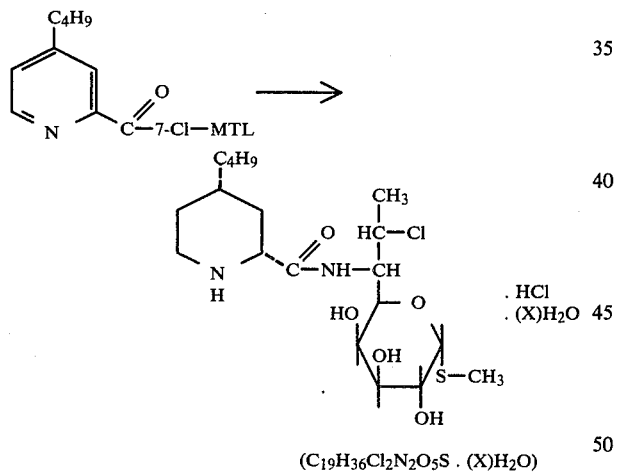

($C_{19}H_{36}Cl_2N_2O_5S$ · (X)H₂O)

Fraction A from the preceding experiment was converted to its HCl salt in the same manner as described for fraction B. A 25–35% yield of product was obtained whose CMR spectrum was essentially identical to that obtained from fraction B.

Preparation 7—Preparation of a Compound in Which the Amino-acid Portion Contains a Heteroatom In a 5-Membered Ring

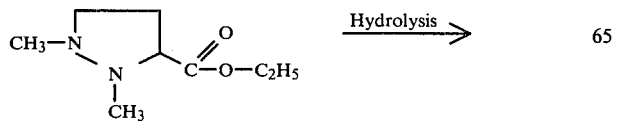

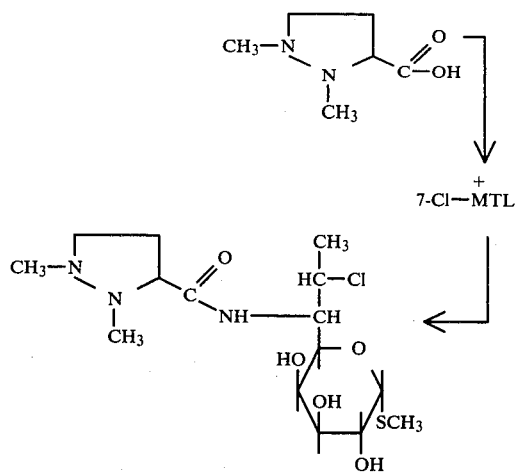

The aminoacid ester (see C.A. 69-67282M) may be hydrolyzed to the free acid by methods well known to those skilled in the art (acid or basic hydrolysis may be used). It may be obtained in the form of the .HCl salt or the zwitterion. The coupling of the aminoacid.HCl with 7-Cl-MTL is accomplished in the same manner as described in Preparation 1, except that 67.7 g (0.357 moles) of the aminoacid is used. After work-up, as described in Preparation 1, the crude product may be purified via chromatography over silica gel and the product fractions combined and converted to the HCl salt.

Preparation 8—Preparation of a Compound in Which the Amino-acid Portion Contains a Heteroatom in a 6-Membered Ring

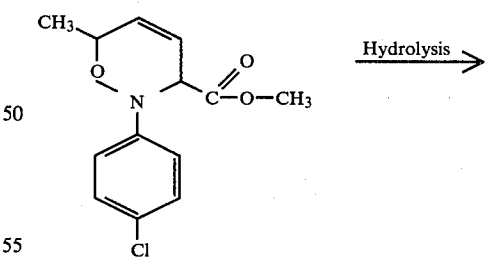

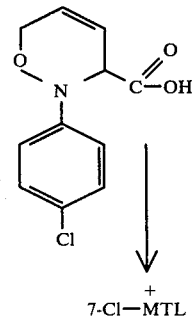

-continued

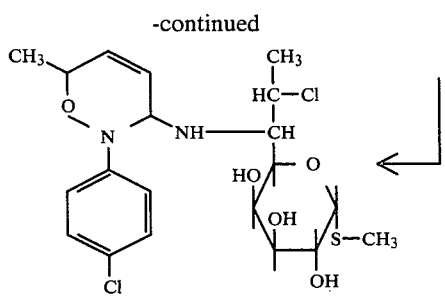

The aminoacid ester (see C.A. 68-59465N) may be hydrolyzed to the free acid by methods well known to those skilled in the art (acid or basic hydrolysis may be used). It may be obtained in the form of the HCl salt or the zwitterion. The coupling of the aminoacid.HCl with 7-Cl-MTL is accomplished in the same manner as described in Preparation 1 except that 103.6 g. (0.357 moles) of the aminoacid is used. After work-up, as described in Preparation 1, the crude product may be purified via chromatography over silica gel and the product fractions combined and converted to the HCl salt.

Preparation 9—2-Phosphate Analogs

The 2-phosphate analog of the compounds prepared in Preparations 1–8 can be prepared by procedures well-known to those skilled in the art. By obvious appropriate modification, the procedure disclosed in U.S. Pat. No. 3,487,068 may be used. Basically, any procedure would first involve the protection of vulnerable groups by methods well-known to those skilled in the art which would then be removed upon completion of the phosphorylation.

Preparation 10—2-Palmitate Analogs

The 2-palmitate analog of the compounds prepared in Preparations 1–8 can be prepared by procedures well-known to those skilled in the art. By obvious appropriate modification, the procedure disclosed in U.S. Pat. No. 3,580,904 may be used. Basically, any procedure would first involve the protection of vulnerable groups by methods well known to those killed in the art which would then be removed upon completion of the acylation with palmitoyl chloride.

The compounds used in the subject invention process exist in the protonated or non-protonated forms according to the pH of the environment. When the protonated form is intended, the compounds exist as pharmaceutically-acceptable acid-addition salts, and when the non-protonated form is intended, the compounds exist as the free base. The free bases can be converted to stable acid-addition salts by neutralizing the free base with the appropriate acid, about pH 7.0, and advantageously to about pH 2 to pH 6. Suitable acids for this purpose include hydrochloric, sulfuric, phosphoric, thiocyanic, fluosilicic, hexafluoroarsenic, hexafluorophosphoric, acetic, succinic, citric, lactic, maleic, fumaric, pamoic, cholic, palmitic, mucic, camphoric, glutaric, glycolic, phthalic, tartaric, lauric, stearic, salicyclic, 3-phenylsalicylic, 5-phenylsalicylic, 3-methylglutaric, orthosulfobenzoic, cyclohexanesulfamic, cyclopentanepropionic, 1,2-cyclohexanedicarboxylic, 4-cyclohexanecarboxylic, octadecenylsuccinic, octenylsuccinic, methanesulfonic, helianthic, Reinecke's, dimethyldithiocarbamic, hexadecylsulfamic, octadecylsulfamic, sorbic, monochloroacetic, undecylenic, 4'-hydroxyazobenzene-4-sulfonic, octadecylsulfuric, picric, benzoic, cinnamic, and like acids. The acidaddition salts can be used for the same purposes as the free base.

The following examples are illustrative of the best mode contemplated by the inventor for carrying out his invention and are not to be construed as limiting.

The examples use U-57,930E or U-60,970E as the active compound and the malarial parasite as the protozoan, but it should be understood that this is only exemplary of the other active compounds of the subject invention in their use as antimalarials and, generally, as antiprotozoans.

Example 1—Capsules

One thousand two-piece hard gelatin capsules for oral use, each containing 250 mg of U-57,930E or U-60,970E, are prepared from the following types and amounts of materials:

| | |
|---|---|
| U-57,930E or U-60,970E | 250 gm |
| Corn starch | 100 gm |
| Talc | 75 gm |
| Magnesium stearate | 25 gm |

The materials are thoroughly mixed and then encapsulated in the usual manner.

The foregoing capsules are useful for the treatment of malaria in adult humans by oral administration of one capsule every 6 hours.

Using the procedure above, capsules are similarly prepared containing U-57,930E or U-60,970E in 10, 25, 50, 100, and 500 mg amounts by substituting 10, 25, 50, 100 and 500 gm of U-57,930E or U-60,970E for the 250 gm used above.

Example 2—Capsules

One thousand two-piece hard gelatin capsules for oral use, each containing 200 mg. of U-57,930E or U-60,970E and 200 mg of hydroxychloroquine sulfate, are prepared from the following types and amounts of ingredients:

| | |
|---|---|
| U-57,930E or U-60,970E | 200 gm |
| Hydroxychloroquine sulfate | 200 gm |
| Talc | 75 gm |
| Magnesium stearate | 25 gm |

The ingredients are thoroughly mixed and then encapsulated in the usual manner.

The foregoing capsules are useful to prevent recurrent attacks of P. vivax, in adult humans by the oral administration of 1 capsule weekly.

Example 3—Tablets

One thousand tablets for oral use, each containing 500 mg of U-57,930E or U-60,970E, are prepared from the following types and amounts of materials:

| | |
|---|---|
| U-57,930E or U-60,970E | 500 gm |
| Lactose | 125 gm |
| Corn Starch | 65 gm |
| Magnesium stearate | 25 gm |
| Light liquid petrolatum | 3 gm |

The ingredients are thoroughly mixed and slugged. The slugs are broken down by forcing through a number 16 screen. The resulting granules are then compressed into tablets, each tablet containing 500 mg of U-57,930E or U-60,970E.

The foregoing tablets are useful for treatment of malarial infections in adult humans by oral administration of one tablet three times a day.

Using the above procedure, except for reducing the amount of U-57,930E or U-60,970E to 250 gm, tablets containing 250 mg of U-57,930E or U-60,970E are prepared.

Example 4—Tablets

One thousand oral tablets, each containing 125 mg of U-57,930E or U-60,970E and 325 mg of quinine sulfate, are prepared from the following types and amounts of materials:

| U-57,930E or U-60,970E | 125 gm |
|---|---|
| Quinine sulfate | 325 gm |
| Lactose | 50 gm |
| Corn starch | 50 gm |
| Calcium stearate | 25 gm |
| Light liquid petrolatum | 5 gm |

The ingredients are thoroughly mixed and slugged. The slugs are broken down by forcing through a number 16 screen. The resulting granules are then compressed into tablets, each containing 125 mg of U-57,930E or U-60,970E and 325 mg of quinine sulfate.

The foregoing tablets are useful for treatment of malaria by the oral administration of two tablets every 8 hours for 7 days, then one tablet three times a day for 7 days.

Example 5—Oral Syrup

One thousand cc of an aqueous suspension for oral use, containing in each 10 cc dose 25 mg of pyrimethamine, 250 mg of U-57,930E or U-60,970E and 500 mg of sulfadiazine is prepared from the following types and amounts of ingredients:

| U-57,930E or U-60,970E | 25 gm |
|---|---|
| Pyrimethamine | 2.5 gm |
| Sulfadiazine | 50 gm |
| Citric acid | 2 gm |
| Benzoic acid | 1 gm |
| Sucrose | 700 gm |
| Tragacanth | 5 gm |
| Lemon oil | 2 cc |
| Deioinzed water, q.s. | 1000 cc |

The citric acid, benzoic acid, sucrose, tragacanth, and lemon oil are dispersed in sufficient water to make 850 cc of solution. The U-57,930E or U-60,970E pyrimethamine and sulfadiazine are stirred into the syrup until uniformly distributed. Sufficient water is added to make 1000 cc.

The composition so prepared is useful in the prophylactic treatment of malaria in adult humans at a dose of 1 tablespoonful (10 cc) weekly.

Example 6—Parenteral Solution

A sterile aqueous solution for intramuscular use, containing 200 mg of U-57,930E or U-60,970E in 1 cc is prepared from the following types and amounts of materials:

| U-57,930E or U-60,970E | 200 gm |
|---|---|
| Lidocaine hydrochloride | 4 gm |
| Methylparaben | 2.5 gm |
| Propylparaben | 0.17 gm |
| Water for injection, q.s. | 1,000 cc |

The ingredients are dissolved in the water and the solution sterilized by filtration. The sterile solution is filled into vials and the vials sealed.

Example 7—Parenteral Preparation

A sterile aqueous composition for intramuscular use, containing in 1 cc 200 mg of U-57,930E or U-60,970E is prepared from the following types and amounts of ingredients:

| U-57,930E or U-60,970E | 200 gm |
|---|---|
| Lactose | 50 gm |
| Water for injection, q.s. | 1,000 cc |

The U-57,930E or U-60,970E and lactose are dispersed in the water and sterilized. The sterile composition, in the amount of 2 cc, is filled aseptically into sterile vials.

Example 8

Following the procedure of each of the preceding Examples 1-7, inclusive, each antimalarially-active compound of the subject invention is substituted in an equivalent amount for the U-57,930E or U-60,970E shown in the example to provide therapeutic properties. Similarly, each of the above free base compounds can be used in the form of a pharmaceutically (or pharmacologically) acceptable acid addition salt, e.g., hydrochloride, sulfate, nitrate, phosphate, citrate, lactate, acetate, tartrate and succinate.

Further, the 2-phosphate and/or 2-palmitate of each of the above antimalarially-active invention compounds can be substituted as the active ingredient to provide compositions having therapeutic properties.

Test results showing the antimalarial efficacy of U-57,930E in comparison with clindamycin HCl (U-21,251F), 4'-pentyl 1'-N-demethyl clindamycin (U-24,729A) and chloroquine (U-8,284) are as follows:

| | In Vivo Results vs. *P. berghei* | | | |
|---|---|---|---|---|
| | MED[1](mg/kg) | | CD$_{50}$[2] (mg/kg) | |
| COMPOUND | Sub. Q[3] | OI | Sub Q | OI |
| U-57,930E | 0.16 | 1.6 | 16 (12–22) | >50 |
| U-21,251F | <20 | — | 53 (46–61) | — |
| U-24,729A | <1.25 | — | 4.7 (3.2–6.9) | — |
| U-8,284 Chloroquine | <5–10 | 12.5 | 11.5 (8.8–15) | 14 |
| Chloroquine (PO$_4$)$_2$ | <5 | — | >20 | — |

[1]MED = Dosage at which median survival time (ST$_{50}$) was increased significantly (p = 0.05) over ST$_{50}$ of untreated controls.
[2]CD$_{50}$ = Median protective dose in mg/kg 95% limits).
[3]Route of administration Anti-Malarial Test (*P. berghei*)

Test method. Male, CF-1 mice (18 to 20 g) were housed in groups of 10 and were infected intraperitoneally with whole blood from mice infected with *P. berghei* 3 days prior to bleeding. A 0.2-ml amount of heparinized blood, diluted 1:10 with saline, served as the inoculum. This volume contained approximately 106 parasites.

At 4 hr postinfection, each group of 10 mice was treated, either subcutaneously with 0.2 ml or orally by gavage, with 0.5 ml of the desired drug concentration. Treatment was continued once each day for 4 days. The animals were observed for 28 days and deaths were recorded. Deaths prior to the 6th day were considered traumatic.

Evaluation for efficacy of the various analogues and drug concentrations of individual analogues was based on the median survival time of animals at each treatment level and the median protective dose of the individual analogue. Calculations were computed on an IBM 370 digital computer. Results based on the treated groups were compared with those of untreated groups or groups treated with chloroquine.

Other protozoans within the concept of the subject invention process are intracellular parasites, for example, the species of Plasmodia, Toxoplasma, and Leishmania; protozoa that digest the red blood cells (RBC's) of treated patients, for example, *Amoeba histolytica* and certain Trypanosoma; and other helminths which injest RBC's during the disease processes, for example, the Schistosomes.

We claim:

1. A method of treating malaria comprising the systemic administration of an effective amount of a compound having the formula

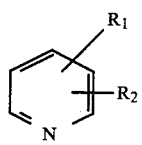

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, —(CH$_2$)$_n$—OH, —(CH$_2$)$_n$—NR$_4$R$_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein $R_2$, which can be singly substituted in any position of the pyridine ring not already substituted by $R_1$, is

and X is the amino function of a compound selected from the group consisting of 7(S)-halo-methyl 1-thio-α-lincosaminide and 7(R)-halo-methyl 1-thio-α-lincosaminide; the 2-phosphate; the 2-palmitate; and the pharmaceutically acceptable acid-addition salts thereof, to a mammal hosting a malarial parasite.

2. A method of treating malaria comprising the systemic administration of an effective amount of a compound having the formula

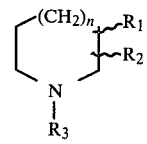

wherein $R_1$ and $R_2$, which can be in the 2, 3, 4, 5, 6, 7, 8, or 9 position of the ring, are as defined in claim 1; wherein $R_3$ is selected from the group consisting of H, CH$_3$, C$_2$H$_5$, and —CH$_2$—CH$_2$—OH; wherein n is an integer of from 1 to 4, inclusive; the 2-phosphate; the 2-palmitate; and the pharmaceutically acceptable acid-addition salts thereof, to a mammal hosting a malarial parasite.

3. A method of treating malaria comprising the systemic administration of an effective amount of a compound, as defined in claim 1, wherein $R_1$ is in the 4-position and is alkyl of from 1 to 8 carbon atoms, inclusive, and isomeric forms thereof; wherein $R_2$ is in the 2 or 3 position; and the pharmaceutically acceptable acid-addition salts thereof, to a mammal hosting a malarial parasite.

4. A method of treating malaria comprising the systemic administration of an effective amount of a compound, as defined in claim 2, wherein $R_1$ is in the 4 position and is alkyl of from 1 to 8 carbon atoms, inclusive, and isomeric forms thereof; and the pharmaceutically acceptable acidaddition salts thereof, to a mammal hosting a malarial parasite.

5. A method of treating malaria comprising the systemic administration of an effective amount of a compound having the formula

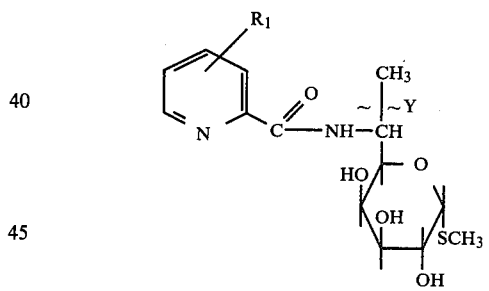

wherein $R_1$, which can be singly or multiply substituted in the 3, 4, 5, or 6 position of the pyridine ring, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, —(CH$_2$)$_n$—OH, —(CH$_2$)$_n$—NR$_4$R$_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein Y is selected from the group consisting of 7(S)-halo and 7(R)-halo; and the pharmaceutically acceptable acid-addition salts thereof, to a mammal hosting a malarial parasite.

6. A method of treating malaria comprising the systemic administration of an effective amount of a compound, as defined in claim 5, wherein Y is 7(S)-halo, and the pharmaceutically acceptable acid-addition salts thereof, to a mammal hosting a malarial parasite.

7. A method of treating malaria comprising the systemic administration of an effective amount of a compound having the formula

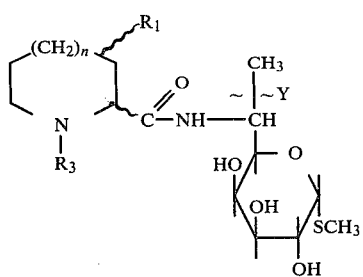

wherein $R_1$, which can be singly or multiply substituted in the 3, 4, 5, 7, 8 or 9 position of the ring, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein $R_3$ is selected from the group consisting of H, $CH_3$, $C_2H_5$, and $-CH_2-CH_2-OH$; wherein n is an integer of from 1 to 4, inclusive, wherein Y is selected from the group consisting of 7(S)-halo and 7(R)-halo; and the pharmaceutically acceptable acid-addition salts thereof, to a mammal hosting a malarial parasite.

8. The method, according to claim 7, wherein 7(S)-halo is 7(S)-chloro.

9. A method of treating malaria comprising the systemic administration of an effective amount of a compound as defined in claim 7 wherein Y is 7(S)-halo; $R_1$ is alkyl of from 1 to 8 carbon atoms, inclusive, and isomeric forms thereof; $R_3$ is hydrogen, and the pharmaceutically acceptable acid-addition salts thereof, to a mammal hosting a malarial parasite.

10. A method, as defined in claim 9, wherein the compound used is as follows: Y is 7(S)-halo; $R_1$ is $C_2H_5$ and $R_3$ is hydrogen.

11. A method, as defined in claim 9, wherein the compound used is as follows: Y is 7(S)-halo; $R_1$ is $C_4H_9$ and $R_3$ is hydrogen.

12. A method, as defined in claim 9, wherein the 7(S)-halo of the compound used is 7(S)-chloro.

13. A process, as defined in claim 10, wherein the 7(S)-halo of the compound used is 7(S)-chloro.

14. A method, as defined in claim 11, wherein the 7(S)-halo of the compound used is 7(S)-chloro.

15. The method of claim 7 wherein from about 0.5 to about 300 mg of compound per kg of host body weight is systemically administered daily in association with a pharmaceutical carrier.

16. The method of claim 7 wherein from about 0.5 to about 200 mg of compound per kg of host body weight is parenterally administered daily in association with a sterile pharmaceutical carrier.

17. The method of claim 7 wherein from about 1 to about 300 mg of compound per kg of host body weight is orally administered daily in association with a pharmaceutical carrier.

18. The method of treating malaria comprising the systemic administration of an effective amount of a compound having the formula

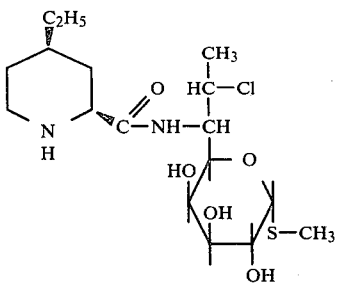

the 2-phosphate; the 2-palmitate; and the pharmaceutically acceptable acid-addition salts thereof, to a mammal hosting a malarial parasite.

19. The method of claim 18 wherein from about 0.5 to about 300 mg of compound per kg of host body weight is systemically administered daily in association with a pharmaceutical carrier.

20. The method of claim 18 wherein from about 0.5 to about 200 mg of compound per kg of host body weight is parenterally administered daily in association with a sterile pharmaceutical carrier.

21. The method of claim 18 wherein from about 1 to about 300 mg of compound per kg of host body weight is orally administered daily in association with a pharmaceutical carrier.

22. A method for treating malaria comprising the systemic administration of an effective amount of a compound having the formula

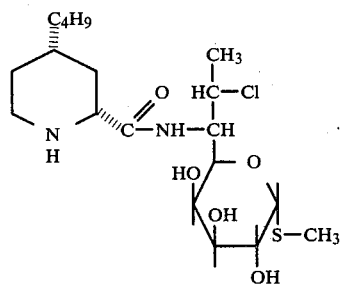

the 2-phosphate; the 2-palmitate; and the pharmaceutically acceptable acid-addition salts thereof, to a mammal hosting a malarial parasite.

23. The method of claim 22 wherein from about 0.5 to about 300 mg of compound per kg of host body weight is systemically administered daily in association with a pharmaceutical carrier.

24. The method of claim 22 wherein from about 0.5 to about 200 mg of compound per kg of host body weight is parenterally administered daily in association with a sterile pharmaceutical carrier.

25. The method of claim 22 wherein from about 1 to about 300 mg of compound per kg of host body weight is orally administered daily in association with a pharmaceutical carrier.

26. A method of treating malaria comprising the systemic administration of an effective amount of a compound having the formula

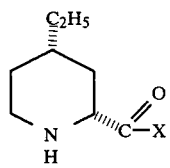

wherein X is selected from the group consisting of 7(S)-halo-methyl 1-thio-α-lincosaminide and 7(R)-halo-methyl 1-thio-α-lincosaminide; the 2-phosphate, the 2-palmitate, and the pharmaceutically acceptable acid-addition salts thereof, to a mammal hosting a malarial parasite.

27. A method of treating malaria comprising the systemic administration of an effective amount of a compound having the formula

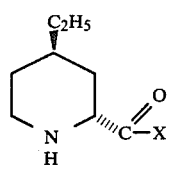

wherein X is as defined in claim 26, the 2-phosphate, the 2-palmitate, and the pharmaceutically acceptable acid-addition salts thereof, to a mammal hosting a malarial parasite.

28. A method of treating malaria comprising the systemic administration of an effective amount of a compound having the formula

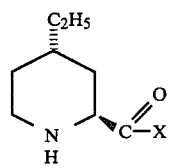

wherein X is as defined in claim 26, the 2-phosphate, the 2-palmitate, and the pharmaceutically acceptable acid-addition salts thereof, to a mammal hosting a malarial parasite.

29. A method of treating malaria comprising the systemic administration of an effective amount of a compound having the formula

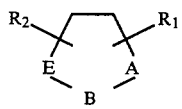

wherein A, B and E are selected from the group consisting of nitrogen, oxygen, sulfur and $CR_1R_1$; $R_1$ and $R_2$ are as defined in claim 1, and can be attached to any ring carbon or nitrogen atom; $R_1$ can be multiply attached to any ring carbon atom, the 2-phosphate, the 2-palmitate, and the pharmaceutically acceptable acid addition salts thereof, to a mammal hosting a malarial parasite.

30. A method of treating malaria comprising the systemic administration of an effective amount of a compound having the formula

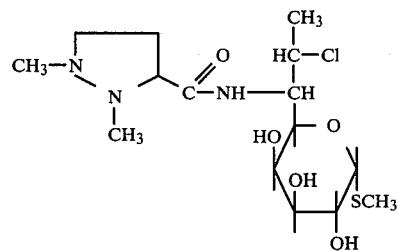

the 2-phosphate; the 2-palmitate; and the pharmaceutically acceptable acid-addition salts thereof, to a mammal hosting a malarial parasite.

31. A method of treating malaria comprising the systemic administration of an effective amount of a compound having the formula

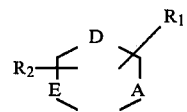

wherein A, B, D and E are selected from the group consisting of nitrogen, oxygen, sulfur and $CR_1R_1$; $R_1$ and $R_2$ are as defined in claim 1, and can be attached to any ring carbon or nitrogen atom; $R_1$ can be multiply attached to any ring carbon atom, the 2-phosphate; the 2-palmitate; and the pharmaceutically acceptable acid addition salts thereof, to a mammal hosting a malarial parasite.

32. A method, according to claim 31, wherein said compound used can be shown by the formula

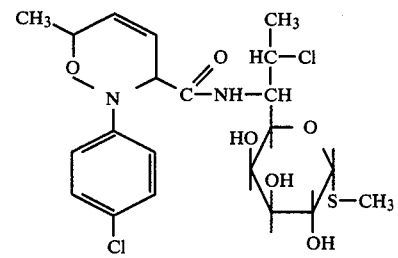

the 2-phosphate; the 2-palmitate; and the pharmaceutically acceptable acid-addition salts thereof.

33. A method of treating a protozoan infection comprising the systemic administration of an effective amount of a compound having the formula

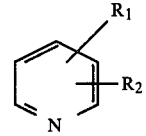

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, $-(CH_2)_n-OH$, —(CH$_2$)$_n$—NR$_4$R$_5$, and isomeric forms thereof, wherein n is an integer of from 1 to 8, inclusive, R$_4$ and R$_5$ are H or alkyl of from 1 to 8 carbon atoms, inclusive, and isomeric forms thereof; wherein R$_2$, which can be singly substituted in any position of the pyridine ring not already substituted by R$_1$, is

and X is the amino function of a compound selected from the group consisting of 7(S)-halo-methyl 1-thio-α-lincosaminide and 7(R)-halo-methyl 1-thio-α-lincosamoinide; the 2-phosphate; the 2-palmitate; and the pharmaceutically acceptable acid-addition saltls thereof, to a mammal hosting a protozoan parasite.

34. A method of treating a protozoan infection comprising the systemic administration of an effective amount of a compound having the formula

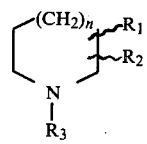

wherein R$_1$ and R$_2$, which can be in th 2, 3, 4, 5, 6, 7, 8, or 9 position of the ring, are as defined in claim 1; wherein R$_3$ is selected from the group consisting of H, CH$_3$, C$_2$H$_5$, and —CH$_2$—CH$_2$—OH; wherein n is an integer of from 1 to 4, inclusive; the 2-phosphate; the 2-palmitate; and the pharmaceutically acceptable acid-addition salts thereof, to a mammal hosting a protozoan parasite.

* * * * *

UNITED STATES PATENT AND TRADEMARK OFFICE
CERTIFICATE OF CORRECTION

PATENT NO. : 4,293,547
DATED : October 6, 1981
INVENTOR(S) : Charles Lewis and Robert D. Birkenmeyer It is certified that error appears in the above—identified patent and that said Letters Patent is hereby corrected as shown below:

Column 16, line 55: "CHLL" should read -- CHCl --
Column 28, lines 38, 42: " 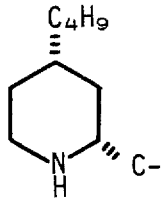 " should read -- 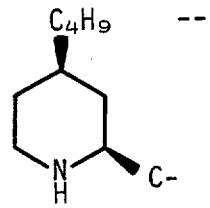 --

Signed and Sealed this

First Day of June 1982

[SEAL]

Attest:

GERALD J. MOSSINGHOFF

Attesting Officer    Commissioner of Patents and Trademarks